US010238288B2

(12) United States Patent
Gupta et al.

(10) Patent No.: US 10,238,288 B2
(45) Date of Patent: Mar. 26, 2019

(54) DIRECT FREQUENCY MODULATING RADIO-FREQUENCY SENSORS

(71) Applicant: Microsoft Technology Licensing, LLC, Redmond, WA (US)

(72) Inventors: Sidhant Gupta, Bellevue, WA (US); Jonathan Lester, Bellevue, WA (US); Vaishnavi Nattar Ranganathan, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 15/624,584

(22) Filed: Jun. 15, 2017

(65) Prior Publication Data

US 2018/0360312 A1 Dec. 20, 2018

(51) Int. Cl.
*A61B 5/00* (2006.01)
*H04Q 9/00* (2006.01)

(52) U.S. Cl.
CPC .......... *A61B 5/0002* (2013.01); *A61B 5/6801* (2013.01); *H04Q 9/00* (2013.01);
(Continued)

(58) Field of Classification Search
CPC ................ A61B 5/0002; A61B 5/6801; A61B 2560/0214; H04Q 9/00; H04Q 2209/40; H04Q 2209/886
(Continued)

(56) References Cited

U.S. PATENT DOCUMENTS 6,295,361 B1 9/2001 Kadansky et al.
7,308,496 B2 12/2007 Yeager et al.
(Continued)

FOREIGN PATENT DOCUMENTS

WO 2008063710 A2 5/2008
WO 2008113425 A1 9/2008
(Continued)

OTHER PUBLICATIONS

Smith, Joshua R., "WISP (Wireless Identification and Sensing Platform)", http://sensor.cs.washington.edu/WISP.html, Retrieved on: Apr. 27, 2017, 2 pages.
(Continued)

*Primary Examiner* — Hirdepal Singh
(74) *Attorney, Agent, or Firm* — Alleman Hall Creasman & Tuttle LLP (57) ABSTRACT

A wearable radio frequency receiver device is provided, which includes a receiver antenna configured to receive an interrogation signal from a transmitter. The receiver device further includes a sensor coupled to the receiver antenna and configured to receive a physiological input from a user wearing the device and generate a sensor signal based on the physiological input, and a modulator configured to perform direct modulation on the received interrogation signal based on the sensor signal to encode the physiological input in the directly modulated interrogation signal. The receiver antenna may be configured to reflect at least a portion of the directly modulated interrogation signal as backscatter radiation. A transceiver including a transceiver antenna may be provided to receive the directly modulated interrogation signal, and the modulation receiver may be configured to process the directly modulated interrogation signal and output a decoded physiological input.

18 Claims, 10 Drawing Sheets

(52) U.S. Cl.
CPC .. *A61B 2560/0214* (2013.01); *H04Q 2209/40* (2013.01); *H04Q 2209/886* (2013.01)

(58) Field of Classification Search
USPC .................................................. 340/870.18
See application file for complete search history.

(56) References Cited

U.S. PATENT DOCUMENTS

| | | | |
|---|---|---|---|
| 7,512,418 | B2 | 3/2009 | Ara et al. |
| 8,615,656 | B2 | 12/2013 | Weinstein et al. |
| 8,954,008 | B2* | 2/2015 | Wang ...................... H04B 1/00 455/119 |
| 8,996,530 | B2 | 3/2015 | LuVogt et al. |
| 9,319,220 | B2 | 4/2016 | Grewal et al. |
| 9,436,812 | B2 | 9/2016 | Chhabra et al. |
| 9,450,298 | B2 | 9/2016 | Lee |
| 9,569,771 | B2 | 2/2017 | Lesavich et al. |
| 9,584,517 | B1 | 2/2017 | Roth et al. |
| 9,820,690 | B1* | 11/2017 | Schwartz ............. A61B 5/4848 |
| 2002/0152044 | A1* | 10/2002 | Shanks ................ G06K 7/0008 702/106 |
| 2002/0154029 | A1* | 10/2002 | Watters ..................... G01D 5/48 340/870.07 |
| 2002/0158775 | A1 | 10/2002 | Wallace |
| 2003/0063742 | A1 | 4/2003 | Neufeld et al. |
| 2004/0120528 | A1 | 6/2004 | Elliott et al. |
| 2005/0070811 | A1 | 3/2005 | Crowley |
| 2006/0149962 | A1 | 7/2006 | Fountain et al. |
| 2009/0215408 | A1* | 8/2009 | Evers ................... G01S 13/758 455/90.1 |
| 2010/0069772 | A1 | 3/2010 | Henke et al. |
| 2010/0327887 | A1 | 12/2010 | Denison et al. |
| 2011/0003610 | A1 | 1/2011 | Key et al. |
| 2012/0159184 | A1 | 6/2012 | Johnson et al. |
| 2013/0002423 | A1* | 1/2013 | Robertson .......... A61B 1/00016 340/539.12 |
| 2013/0099918 | A1* | 4/2013 | Dunst ................ G08B 21/0211 340/539.12 |
| 2013/0254290 | A1 | 9/2013 | Grossman |
| 2014/0200424 | A1 | 7/2014 | Etzkorn et al. |
| 2014/0317686 | A1 | 10/2014 | Vetillard |
| 2014/0365507 | A1 | 12/2014 | Wissner et al. |
| 2015/0112918 | A1 | 4/2015 | Zheng et al. |
| 2015/0148634 | A1* | 5/2015 | Garudadri .......... A61B 5/02141 600/323 |
| 2015/0262069 | A1 | 9/2015 | Gabriel et al. |
| 2015/0310424 | A1 | 10/2015 | Myers |
| 2015/0347768 | A1 | 12/2015 | Martin et al. |
| 2015/0356524 | A1 | 12/2015 | Pennanen |
| 2015/0363280 | A1* | 12/2015 | Yeager ..................... A61B 5/00 711/103 |
| 2016/0006754 | A1 | 1/2016 | Woodward et al. |
| 2016/0011091 | A1 | 1/2016 | Huang et al. |
| 2016/0036826 | A1 | 2/2016 | Pogorelik et al. |
| 2016/0086175 | A1 | 3/2016 | Finlow-bates et al. |
| 2016/0098730 | A1 | 4/2016 | Feeney |
| 2016/0120473 | A1 | 5/2016 | Linton et al. |
| 2016/0260169 | A1 | 9/2016 | Arnold et al. |
| 2016/0261690 | A1 | 9/2016 | Ford |
| 2016/0292672 | A1 | 10/2016 | Fay et al. |
| 2016/0350534 | A1 | 12/2016 | Poomachandran et al. |
| 2017/0000390 | A1* | 1/2017 | Biederman ........... A61B 5/6833 |
| 2017/0006003 | A1 | 1/2017 | Zakaria et al. |
| 2017/0048217 | A1 | 2/2017 | Biggs et al. |
| 2017/0111175 | A1 | 4/2017 | Oberhauser et al. |
| 2017/0127155 | A1* | 5/2017 | Zheng ...................... H04Q 9/00 |
| 2017/0286820 | A1* | 10/2017 | Nikunen ............ G06K 19/0723 |
| 2018/0085605 | A1* | 3/2018 | Maharbiz ............. A61B 8/0808 |

FOREIGN PATENT DOCUMENTS

| | | |
|---|---|---|
| WO | 2013011263 A1 | 1/2013 |
| WO | 2014105914 A1 | 7/2014 |
| WO | 2016020465 A1 | 2/2016 |
| WO | 2016154209 A1 | 9/2016 |
| WO | 2017007725 A1 | 1/2017 |
| WO | 2018090012 A1 | 5/2018 |

OTHER PUBLICATIONS

Ma, Michelle., "No-power Wi-Fi connectivity could fuel Internet of Things reality", http://www.washington.edu/news/2014/08/04/no-power-wi-fi-connectivity-could-fuel-internet-of-things-reality/, Aug. 4, 2014, 9 pages.

"Blockchain as a Service", Retrieved from: https://www.cccinnovationcenter.com/wp-content/uploads/2017/01/Blockchain-DCSummit.pptx, May 12, 2017, 17 Pages.

"Intel Software Guard Extensions", Retrieved from: https://download.01.org/intel-sgx/linux-1.7/docs/Intel_SGX_Developer_Guide.pdf, May 27, 2017, 34 pages.

"iOS_Security_iOS_10_Mar2017", in White Paper of iOS Security, Mar. 2017, 68 Pages.

"Tendermint Added to Azure", Retrieved from: http://www.coindesk.com/press-releases/tendermint-added-to-azure/,, Mar. 18, 2016, 2 Pages.

"Thoughts on UTXOs by Vitalik Buterin", Retrieved from: https://medium.com/@ConsenSys/thoughts-on-utxo-by-vitalik-buterin-2bb782c67e53, Mar. 9, 2016, 5 Pages.

"Working with the Secure Enclave", Retrieved from: https://developer.apple.com/library/content/documentation/Security/Conceptual/CertKeyTrustProgGuide/SecureKeyGen.html, May 17, 2017, 3 Pages.

"U.S. Appl. No. 15/592,697", filed May 11, 2017, 41 Pages.
"U.S. Appl. No. 15/592,750", filed May 11, 2017, 37 Pages.
"U.S. Appl. No. 15/592,802", filed May 11, 2017, 41 Pages.
"U.S. Appl. No. 15/592,867", filed May 11, 2017, 47 pages.
"U.S. Appl. No. 15/592,928", filed May 11, 2017, 44 Pages.
"U.S. Appl. No. 15/593,001.", filed May 11, 2017, 47 pages.
"U.S. Appl. No. 15/632,247", filed Jun. 23, 2017, 54 Pages.
"U.S. Appl. No. 62/505,038", filed May 11, 2017, 47 pages.

Beekman, Jethro Gideon., "Improving Cloud Security using Secure Enclaves", in Technical Report No. UCB/EECS-2016-219, Dec. 22, 2016, 72 Pages.

Betts, Beth, "Anatomy of a Smart Contract", Retrieved from: https://www.blockchain-expo.com/2017/02/blockchain/anatomy-smart-contract/, Feb. 14, 2017, 12 Pages.

Croman, et al., "On Scaling Decentralized Blockchain", in Proceedings of International Conference on Financial Cryptography and Data Security, Feb. 2016, 16 Pages.

Gidney, Kevin, "Intelligent Contracts—Is This the Way Forward for Enterprises?", Retrieved from: https://www.law.com/corpcounsel/almID/1202774474477/Intelligent-ContractsIs-This-the-Way-Forward-for-Enterprises-/?slreturn=20180812010017, Dec. 12, 2016, 7 Pages.

Gray, Marley, "Bletchley—the Cryptlet Fabric & Evolution of blockchain Smart Contracts", Retrieved from: http://www.dataarchitect.cloud/bletchley-the-cryptlet-fabric-evolution-of-blockchain-smart-contracts/, Feb. 9, 2017, 18 Pages.

Gray, et al., "Project Bletchley—the Cryptlet Fabric", Retrieved from: Retrieved from: https://github.com/Azure/azure-blockchain-projects/blob/master/bletchley/CryptletsDeepDive.md, Nov. 10, 2016, 18 Pages.

Kosba, et al., "Hawk: The Blockchain Model of Cryptography and Privacy-Preserving Smart Contracts", in Proceedings of IEEE Symposium on Security and Privacy, May 22, 2016, 32 Pages.

Lind, et al., "Teechan: Payment Channels Using Trusted Execution Environments", in Journal of Computing Research Repository, Dec. 2016, 14 Pages.

Lohstroh, Marten, "Nov. 3: SGX", in Publication of Security in Computer Systems, 2015, 6 Pages.

Nagpal, Praveen, "Developing Smart Contracts Using Solidity",Retrieved from: https://www.chainthat.com/updates/2017/1/4/developing-smart-contracts-using-solidity, May 30, 2016, 3 Pages.

Ojha, Varun, "Writing Blockchain chaincode in Go for Hyperledger Fabric v0.6", Retrieved from: https://www.ibm.com/developerworks/cloud/library/cl-ibm-blockchain-chaincode-development-using-golang/index.html, Mar. 1, 2017, 14 Pages.

(56) References Cited

OTHER PUBLICATIONS

"International Search Report & Written Opinion for PCT Patent Application No. PCT/US18/027001", dated Jun. 15, 2018, 11 Pages.

"International Search Report & Written Opinion for PCT Patent Application No. PCT/US18/027208", dated Jul. 6, 2018, 12 Pages.

"International Search Report & Written Opinion for PCT Patent Application No. PCT/US18/027210", dated Jul. 10, 2018, 13 Pages.

"International Search Report & Written Opinion for PCT Patent Application No. PCT/US18/027211", dated Jul. 24, 2018, 13 Pages.

Tandulwadikar, Akhil, "Blockchain in Banking: A Measured Approach", in White Paper of Cognizant, Apr. 2016, 10 Pages.

Watanabe, et al., "Blockchain Contract: A Complete Consensus using Blockchain", in Proceedings of IEEE 4th global Conference on Consumer Electronics, Oct. 27, 2015, pp. 577-578.

Wood, Gavin, "Ethereum: A Secure Decentralised Generalised Transaction Ledger Final Draft—Under Review", Retrieved from: https://bravenewcoin.com/assets/Whitepapers/Ethereum-A-Secure-Decentralised-Generalised-Transaction-Ledger-Yellow-Paper.pdf, Aug. 6, 2015, 29 pages.

Zhang, Fan, et al., "Town Crier: An Authenticated Data Feed for Smart Contracts", International Association for Cryptologic Research, Feb. 19, 2016, 23 Pages.

"International Search Report & Written Opinion Issued in PCT Application No. PCT/US2018/034251", dated Aug. 28, 2018, 15 Pages.

\* cited by examiner

DIRECT FREQUENCY MODULATING RADIO-FREQUENCY SENSORS

BACKGROUND

Wireless sensor technology is a rapidly expanding field in which recent research and development have been concentrated in the field of IOT (Internet of Things) devices, which are miniaturized devices incorporating computers coupled with sensors, many of them requiring complicated circuitry and battery storage. While active sensor devices using battery power are often bulky and expensive, passive sensor devices have shown promise due to their small form factor and low production costs. Passive sensor devices harvest power from electromagnetic waves transmitted by a transmitter, and use backscatter to send information back to the transmitter, thereby resulting in a battery-free operation.

SUMMARY

To address these issues, a wearable radio frequency receiver device is provided, which includes a receiver antenna configured to receive an interrogation signal from a transmitter. The receiver device further includes a sensor coupled to the receiver antenna and configured to receive a physiological input from a user wearing the device and generate a sensor signal based on the physiological input, and a modulator configured to perform direct modulation on the received interrogation signal based on the sensor signal. The receiver antenna is configured to reflect at least a portion of the directly modulated interrogation signal as backscatter radiation. Further, a transceiver including a transceiver antenna may be provided to receive the directly modulated interrogation signal, and a processor of the transceiver may be configured to process the directly modulated interrogation signal and output a decoded physiological input.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

Biomedical sensors measure various physiological signs of patients, including body temperature, heart rate, respiratory rate, and blood pressure, blood oxygen saturation via pulse oximetry, blood sugar level, etc. During a clinical visit, typically each of these physiological signs is measured by a clinician using a different measurement procedure, and using various medical instruments. In some settings, such as during hospital stays or using at-home monitoring technology, these signs can be monitored using portable sensors connected by wires to monitoring machines. The inventors have recognized drawbacks with using wired sensors, including increased clutter and the possibility for inadvertent disconnection of the sensor from the monitoring machine. Sterilization of the sensors and cords themselves is also problematic. Standards exist for wireless communication, such as BLUETOOTH®, WIFI, and RFID, however, the inventors have recognized that each of these standards has significant power and computing requirements, that increase the size, complexity, and cost of a biomedical sensor employing one of these standards. Thus, despite the availability of various wireless communications standards, challenges remain to the development of inexpensive, disposable, wearable sensor devices that may have a wide application as consumer health wearables and biomedical devices, for example.

Figure 1:
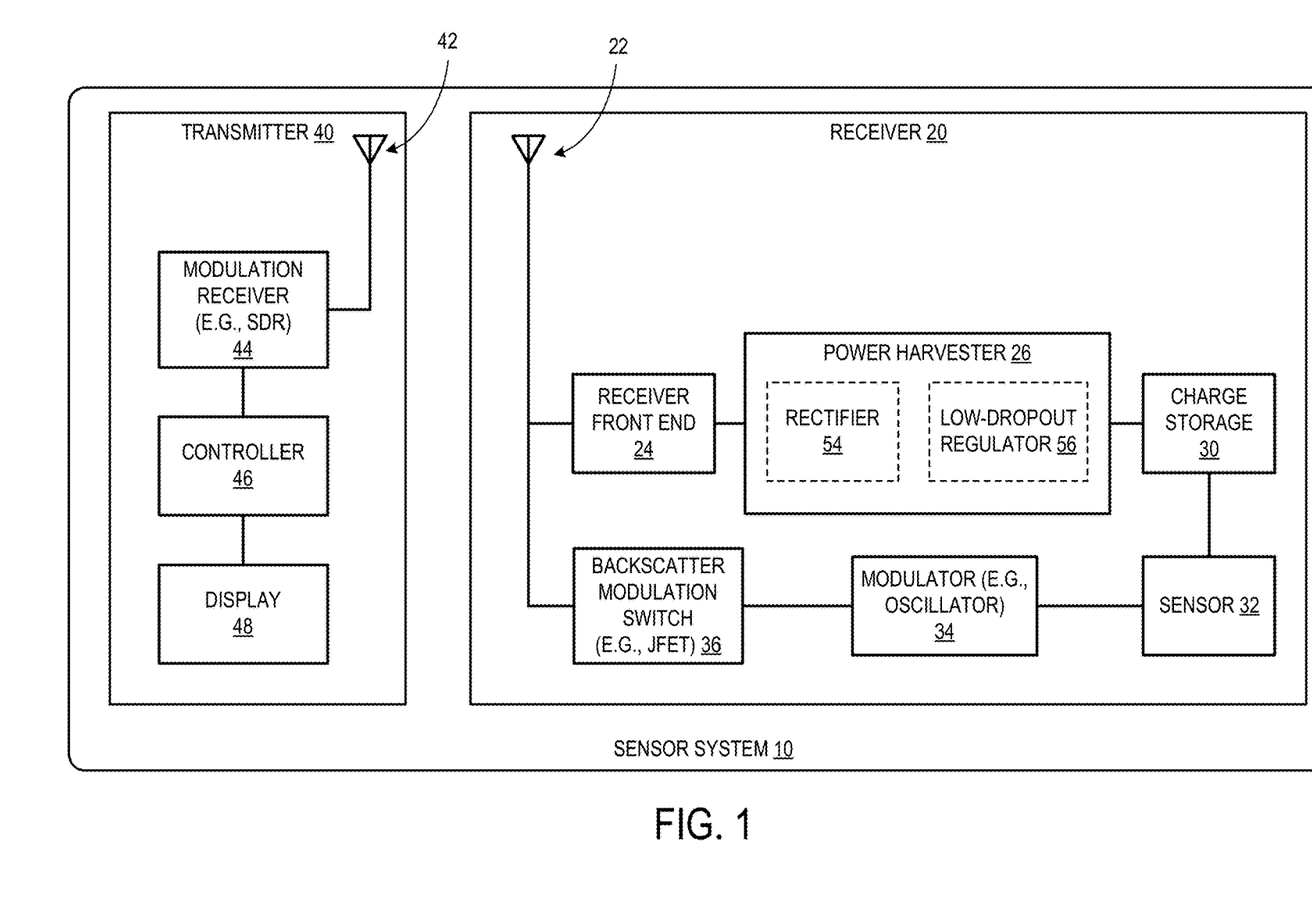
FIG. 1 shows a sensor system according to a first implementation of the present disclosure.
Figure 4A:
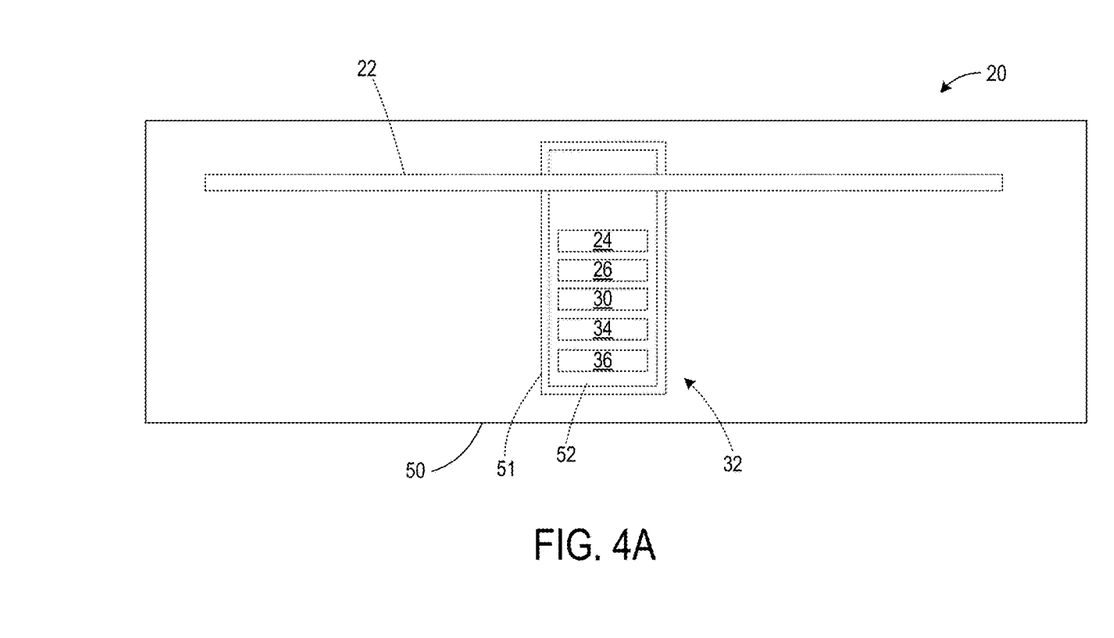
FIG. 4A shows a top view of a receiver sensor device of the second implementation according to one example of the present disclosure.
Figure 4B:
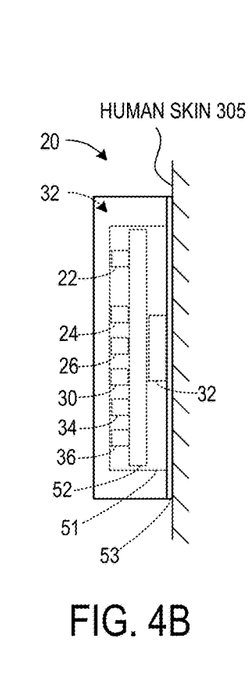
FIG. 4B shows a side view of the receiver sensor device of the second implementation according to one example of the present disclosure.

FIG. 1 illustrates a passive sensor system 10 according to a first implementation of the present disclosure, which has been conceived to address the issues discussed above. As shown, the sensor system 10 comprises a receiver device 20 and a transmitter 40. The receiver device 20, which may also be referred to as a passive receiver sensor device 20, includes a receiver antenna 22, an analog sensor 32, and a modulator 34. The transmitter 40 includes a transmitter antenna 42, a modulation receiver 44 such as a software defined radio (SDR), a controller 46, and a display 48. Alternatively, instead of an SDR, the transmitter 40 may include a frequency modulation receiver that is tuned to receive the modulated backscattered interrogation signal in the band of interest from the receiver device 20. Amplitude or phase modulation receivers may also be utilized as modulation receiver 44. Since transmitter 40 is also configured to receive a backscatter signal from the receiver device 20, it may also be referred herein as a transceiver. The receiver 20 may be a medical wearable or consumer wearable configured as a skin patch, wrist band, arm band, clothing patch, or smart fabric, for example, even utilizing 3-D printing technology to customize a shape or form of the wearable device 20 to adapt to a user or form a specific 3-D shape to exploit new behaviors specific to the 3-D shape, for example. One example form factor for the receiver 20 is illustrated in FIGS. 4A and 4B. The sensor 32 receives a physiological input from a user wearing the receiver device 20, and generates a sensor signal based on the physiological input.

The modulator 34 performs direct modulation on the received interrogation signal based on the sensor signal. The direct modulation may involve frequency modulation, amplitude modulation, or phase modulation, for example. In the illustrated circuits of FIGS. 5A-5E, frequency modulation is employed, and in particular, the frequency modulation is accomplished by frequency-shift keying (FSK). In this implementation, the modulator is a Voltage-Controlled Oscillator (VCO) configured to control an oscillation frequency of the received interrogation signal based upon a sensor signal from a sensor, discussed below. However, it will be noted that in other implementations, the modulator may be configured as a current controlled oscillator that allows any resistive sensor to be connected, or alternatively configured as a current to voltage bridge. In this manner, the physiological input is encoded in the directly modulated interrogation signal, and the receiver antenna is configured to reflect at least a portion of the directly modulated interrogation signal as backscatter radiation. It will be appreciated that while the receiver device 20 may use FSK for encoding, the backscatter translates to amplitude variation at the base-band frequency (encoding frequency) due to the switching of a backscatter modulation switch 36 described below.

Figure 3:
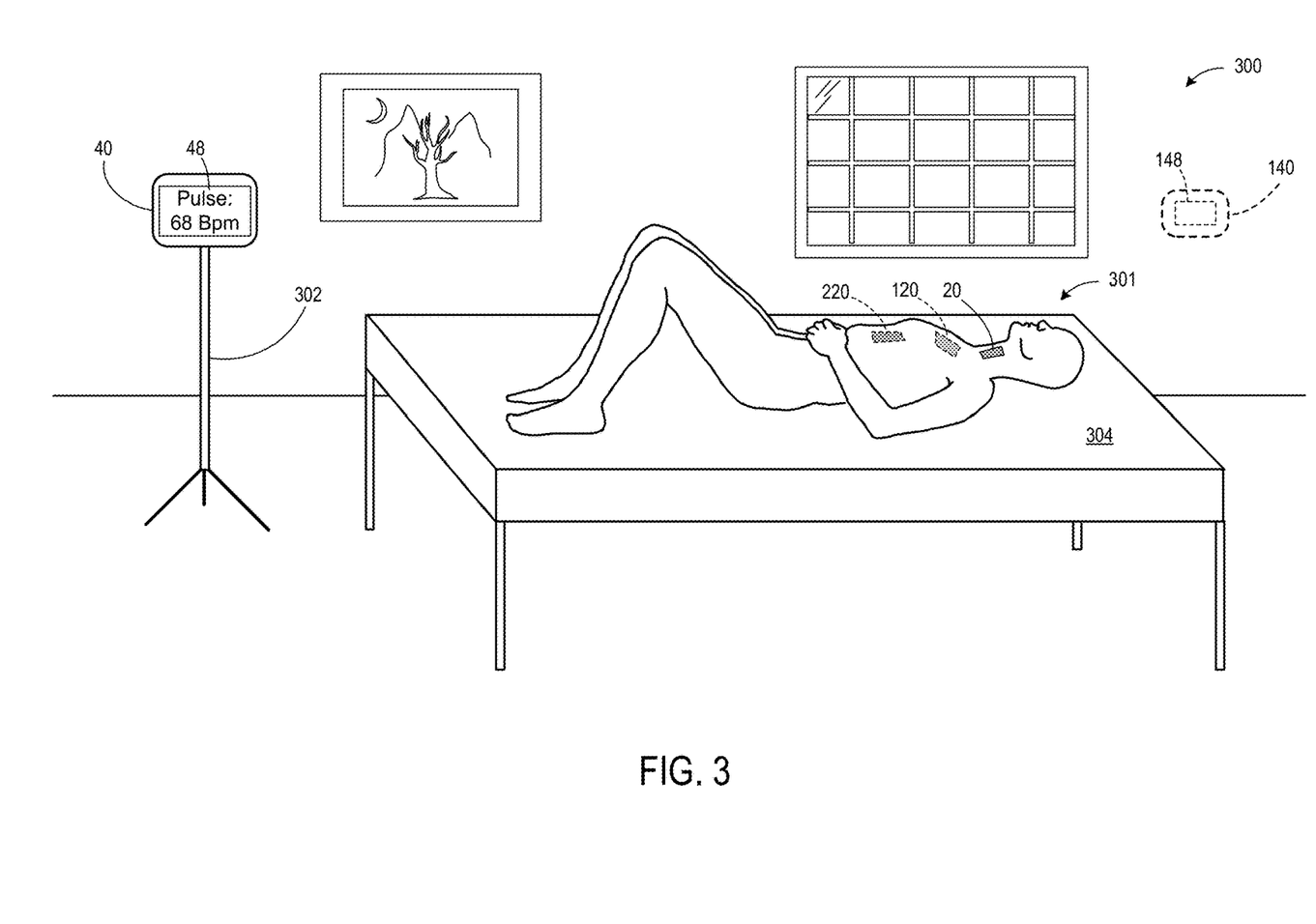
FIG. 3 shows a user implementing a sensor system of the first and/or second implementations according to an example of the present disclosure.

The transceiver antenna is configured to receive the directly modulated interrogation signal and the modulation receiver is configured to process the directly modulated interrogation signal and output a decoded physiological input, as shown at display 48 in FIG. 3. Alternatively, phase-shift keying or amplitude shift keying may be used to encode the physiological input from the sensor into the backscattered portion of the modulated interrogation signal.

The transmitter 40 is configured to be a portable device to be used in proximity to the receiver 20 worn by the user. The modulation receiver 44 is executed on a processor of a controller 46 with non-volatile memory. The modulation receiver 44 causes the transmitter antenna 42 of the transmitter 42 to transmit an interrogation signal at a predetermined radio frequency.

The receiver antenna 22 may be configured as a self-induction circuit that resonates at a predetermined radio frequency of the interrogation signal that is transmitted by the transmitter 40. The self-induction circuit may be configured as a parallel-resonant circuit whose resonant frequency corresponds to a frequency of the interrogation signal transmitted by the transmitter 40. The receiver antenna 22 may be configured as a coil or broadband antenna that is tuned when worn on a human body, and de-tuned when not worn on a human body. When the self-induction circuit resonates at the predetermined radio frequency, the circuitry of the receiver 20 is energized, thereby providing electrical power to each of the individual components of the receiver 20, including the sensor 32 and the backscatter modulation switch 36. The antenna 22 may also be coupled to a rectifier 54, which rectifies the electrical current induced at the self-induction circuit of the receiver antenna 22, converting alternating current to direct current.

As the circuit of the receiver 20 is energized, the sensor 32 is provided with sufficient electrical power to produce an analog electrical sensor signal. The sensor 32 may be configured as a variable impedance sensor, which may be one of a force-sensitive sensor, strain gauge, a resistive sensor, and a capacitive pressure sensor, for example. Alternatively, the sensor may be configured as a variable capacitance, variable voltage, variable resistance or variable current sensor, for example. When configured as a force-sensitive sensor, strain gauge, resistive sensor, or a capacitive pressure sensor, the sensor 32 may generate a sensor signal of a human pulse or concussive impact on human skin, for example. Such an implementation has practical advantage as a pulse sensor or concussion sensor. However, it will be appreciated that the variable impedance sensor is not particularly limited, and may alternatively be configured as a temperature sensor, chemical sensor, microphone, motion sensor, accelerometer, light sensor, pulse oximetry sensor, or skin electrodes, breathing and chest movement sensor, for example. The impedance of the sensor 32 varies as the sensor 32 generates a sensor signal (pressure data, plethysmographic data, electrical data, temperature data, chemical data, or audio data, for example), based on a physiological input of a user. The receiver antenna 22 is then configured to reflect the directly modulated interrogation signal to the transmitter 40. The transmitter antenna 42 of the transmitter 40 then receives the directly modulated interrogation signal, and the modulation receiver 44 demodulates the directly modulated interrogation signal and decodes the sensor information that was modulated inside the sensor signal by the modulator 34. A processor of the controller 46 processes the analog sensor information into digital sensor information, which the controller 46 causes to be displayed on the display 48.

The backscatter modulation switch 36 may configured preferably as a junction field effect transistor (JFET) or alternatively as a metal-oxide-semiconductor field-effect transistor (MOSFET), for example. The JFET 36 may be provided on an integrated circuit such as an ASIC, for example. The JFET 36 may include a gate terminal coupled to the receiver antenna 22 through an impedance matching circuit comprising a matching network filter. The JFET 36 may operate as a switch to configure the dipole antenna 22 between open and short configurations. When the antenna 22 is receiving, the JFET 36 is in an open configuration and allows for the interrogation signal to reach the sensor 32 from the receiver antenna 22, which is tuned to receive at the resonant frequency. During backscatter, the JFET 36 allows for the direct frequency modulated interrogation signal with sensor information to be transmitted from the sensor 32 to the transmitter 40 via the receiver antenna 22 by switching between the open and short configurations. The backscatter modulator switch 36 may be configured as a UHF modulation switch, for example, so that the transmitter 40 and the receiver 20 can communicate with each other at a UHF frequency. Time domain multiplexing may be used for bi-directional backscatter. A low-dropout regulator 56 may also be configured to regulate the output voltage used to power the sensor when necessary and to reduce switching noise. Various other frequencies may be utilized, in other implementations.

Depending on the sensor 32 that is incorporated into the receiver 20, the receiver 20 circuitry may optionally also include a receiver front end 24, a power harvester 26, and a charge storage 30. The receiver front end 24 may include a band-pass filter to reduce strong out-of-band signals and image frequency response, a radiofrequency amplifier configured to increase the sensitivity of the receiver 20 by amplifying weak signals without contaminating them with noise, a local oscillator configured to generate a radio frequency signal at an offset from the incoming interrogation signal, and/or a mixer configured to mix the interrogation signal with a signal from the local oscillator to convert the direct frequency modulated signal to the intermediate frequency. A charge storage 30 such as a capacitor may be configured to store energy generated when the circuit is energized by the interrogation signal. A battery may also be used in the charge storage 30 for circuits and sensor, and higher operational requirements that necessitate more power than that can be harvested from the RF energy. The charge storage 30 may be operatively coupled to the sensor 32 via a power harvester 26 and configured to harvest electrical power from the interrogation signal and at least temporarily store the electrical power, to thereby provide electrical power to the sensor. The power harvester 26 is configured to harvest energy from the interrogation signal, and store it at least temporarily in the charge storage 30. One or more capacitors or batteries may also be provided as the charge storage 30 accessible to the power harvester 26. In other implementations the power harvester may be configured to harvest kinetic energy, for example, when a user's body moves while wearing the receiver 20, light energy from the sun or other light sources, and heat energy from the users body or environment, for example.

Figure 2:
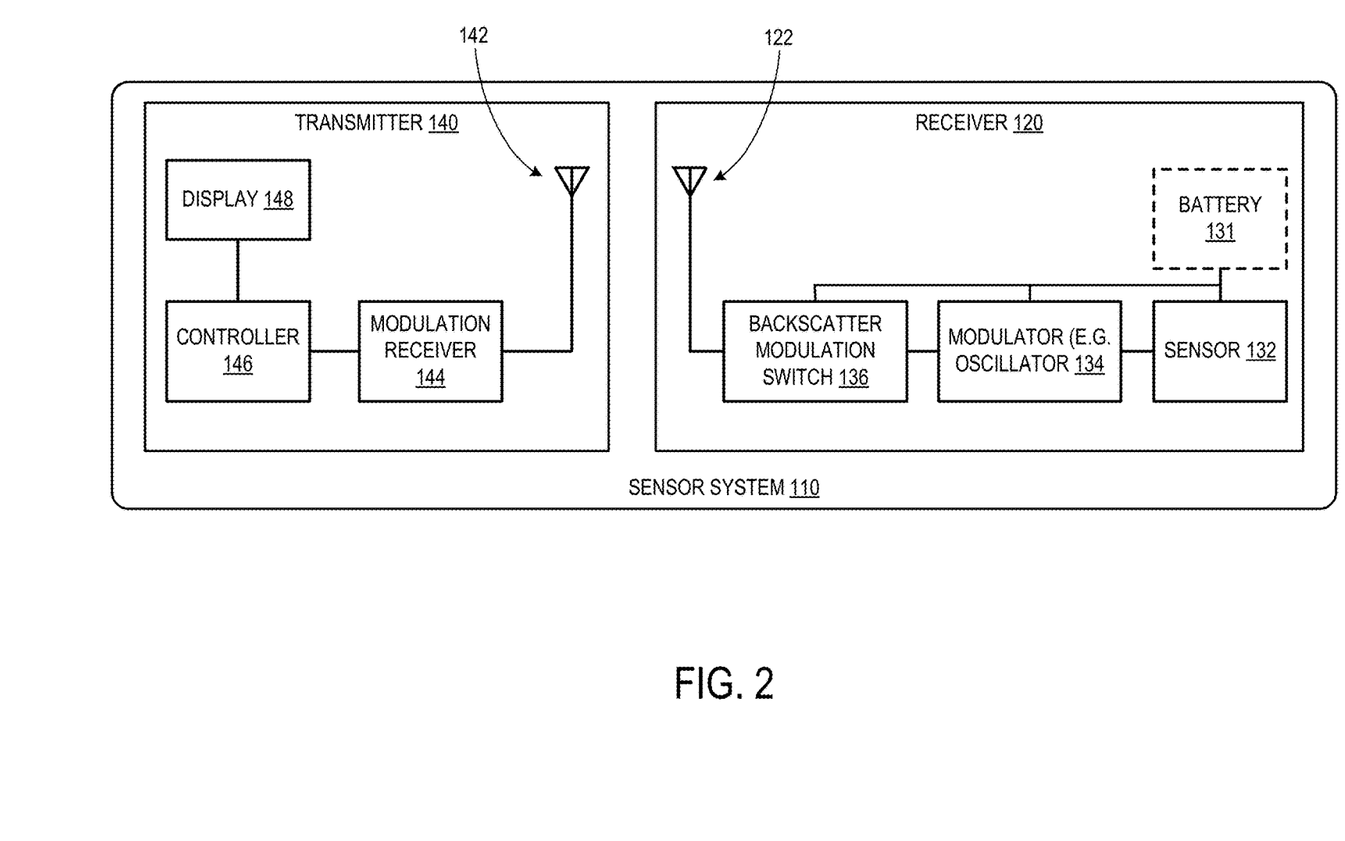
FIG. 2 shows a sensor system according to a second implementation of the present disclosure.

FIG. 2 illustrates an active (e.g., powered) sensor system 110 according to a second implementation of the present disclosure. As shown, the sensor system 110 comprises a receiver device 120 and a transmitter 140. The receiver device 120, which may also be referred to as an active receiver sensor device 120, may comprise a receiver antenna 122, a sensor 132, a modulator 134, and a backscatter modulation switch 136. The transmitter 140 may comprise a transmitter antenna 142, a modulation receiver 144, a controller 146, and a display 148. Since the active sensor system 110 of the second implementation is generally similar to that of the first implementation with the exception of the configuration of the sensor 132 and the absence of a receiver front end, charge storage, and power harvester, the detailed description thereof is abbreviated here for the sake of brevity. It is to be noted that like parts are designated by like reference numerals throughout the detailed description and the accompanying drawings. In the second implementation, the sensor 132 optionally includes a small battery 131 to supplement the electrical energy that is produced when the receiver antenna 122 resonates at a predetermined radio frequency of an interrogation signal that is transmitted by the transmitter 140. In accordance with this configuration, the sensor 132 is provided with supplemental electrical energy to perform its functions, even if the receiver antenna 122 fails to be energized by an interrogation signal. Thus, versatility of the receiver sensor device 120 is increased, albeit at the expense of increased production costs and added weight of the included battery.

FIG. 3 is an example illustration of a user 301 utilizing the passive sensor systems 10, 110 described above. The user 301 may be lying down on a bed 304 or examination table in a room 300 wearing a passive receiver device 20 and/or an active receiver device 120 on the body of the user 301. The number of receiver devices that the user 301 can wear is not particularly limited, and the user 301 may wear any combination of multiple passive and/or active devices depending on the use scenario. In this example, the user is wearing a first receiver device 20, a second receiver device 120, and a third receiver device 220. A transmitter 40 or 140 may be mounted on a stand 302 or placed on a bedside table, for example. The transmitter 40 may alternatively be mounted on a wall or fixed on any other suitable structure in the room 300 in close proximity to the user 301 and the user's passive receiver device 20 and/or active receiver device 120.

In one use case scenario, a user 301 may be lying down on a bed 304 or examination table to perform a sleep study to detect sleep apnea events, for example. The user 301 may place motion sensor devices 120, 220 on the chest and abdomen, respectively, to monitor breathing. The user 301 may also place a microphone device 20 on the upper airway on the trachea, for example, to monitor breathing sounds. These sensor devices 20, 120, and 220 may be wirelessly coupled to a transmitter 40 that is mounted to a stand 302, mounted on a wall, or placed on a bedside table as a base station, for example, in close proximity to the user 301 within the room 300. Although not illustrated, other wireless sensors may be placed on the user 301 as well—a pulse oximeter to measure oxygen saturation, movement sensors on each leg, EEG sensors to measure brain activity, and a nasal pressure transducer in the nostrils, for example. The receiver antennas of each of the multiple sensor devices may have different predetermined resonant frequencies at which the respective receiver antennas are energized to provide electrical energy to the sensors. The transmitter 40 or 140 may also be configured with beamforming or MIMO (multiple-input and multiple-output) technology to enhance the transmission of interrogation signals to each of the multiple wireless sensor devices.

Within each wireless sensor device, additional side channels may be used for communication, control, actuation, and calibration. The transmitter 40 may be controlled to transmit interrogation signals of multiple frequencies to be received by different side channels within each receiver sensor device 20, 120, 220 performing different functions (for example, a positioning receiver device that is specialized for position, and a calibration receiver device that is specialized for calibration, for example). The side channels may also be implemented by adding in other antennas in the same sensor device.

A display 48 on the transmitter 40 displays information about the vital signs of the user 301 so that a health professional may monitor the live data stream from each of the sensors while the user 301 sleeps on the bed 304 or examination table. The collected data from each of the sensors may be stored in a memory of the transmitter 40 to be analyzed later by a health professional to diagnose apnea and hypopnea events during the sleep of the user 301. In accordance with this example, a user 301 may conduct a sleep study that approximates a clinical polysomnography test (PSG) at home without visiting a clinic or sleep laboratory. The costs of production of the receivers may be kept down, so that the entire sensor system is kept affordable for the average consumer who may want to conduct a sleep study in the comfort of one's own home. The wireless sensors do not need to be connected to the transmitter via wires, thereby increasing the comfort of a user 301 undergoing the sleep study.

FIGS. 4A-B illustrate an example receiver sensor device 20 according to the first implementation of the present disclosure. FIG. 4A depicts a top view of the device 20 as it would be viewed by a user mounting the device 20 on the skin 305. FIG. 4B depicts a side view of the device 20. The receiver sensor device 20 has an elongated form factor with a pad 50 having an adhesive layer 51, the pad being configured to extend in the same directions as the antennas 22, which are embedded within the pad 50 and operatively coupled to a sensor 32. The pad 50 is provided on a back surface of the sensor device 20 and configured to adhere onto the user's skin 305 or clothing via the adhesive layer 51 on the back side of the pad 50. The pad 50 and antennas 22 may be provided with sufficient flexibility to be bent comfortably around a wrist, neck, or chest of the user, for example. The pad 50 may be formed to completely encompass the circuit board 52 to which the various electrical components such as receiver antenna 22, receiver front end 24, power harvester 26, charge storage 30, sensor 32, modulator 34, and backscatter modulation switch 36 are mounted. It will be appreciated that the pad 50 functions as a flexible substrate to which the receiver antenna, sensor, and modulator are coupled by the printed circuit board (which itself may be flexible).

A packaging 53, such as a plastic container, may be formed to surround the electrical components mounted to the circuit board 52. It will be appreciated that the sensor 32 is mounted to the circuit board so as to have a sensing end of the sensor 32 face the user's skin 305, when the pad 50 is adhered to the skin 305 or clothing of the user. In some examples, electrodes of the sensor 32 may be disposed within the adhesive pad 50 such that the electrodes make direct contact with the skin 305 when the sensor device 20 is worn by the user. Although not illustrated, an access opening may be provided in the pad to enable the electrical components to be placed therein during manufacture, or during use, for example to change batteries of the sensor. It will also be noted that the form factor of FIGS. 4A-B may also be applied to the active sensor system depicted in FIG. 2. Further, it should be appreciated that the form factor of FIGS. 4A-4B is merely illustrative, and various other form factors may be utilized.

Figure 5A:
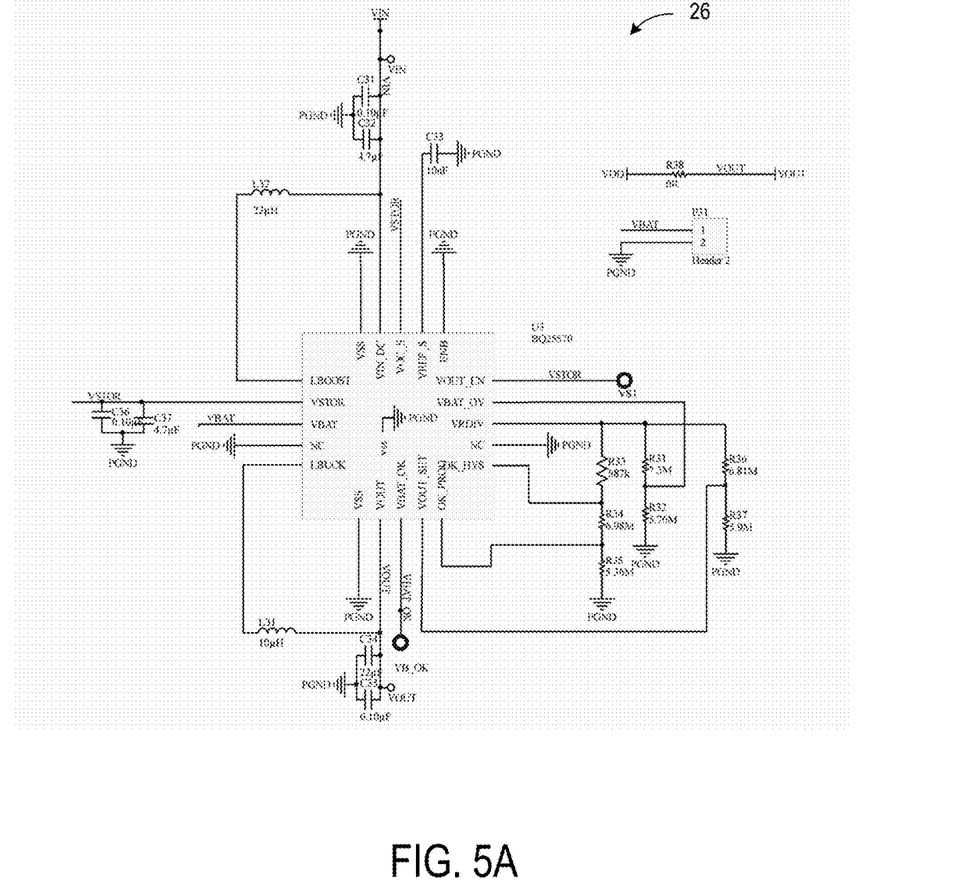
FIG. 5A shows a circuit diagram of the power harvester of the receiver sensor device of the second implementation according to one example of the present disclosure.
Figure 5B:
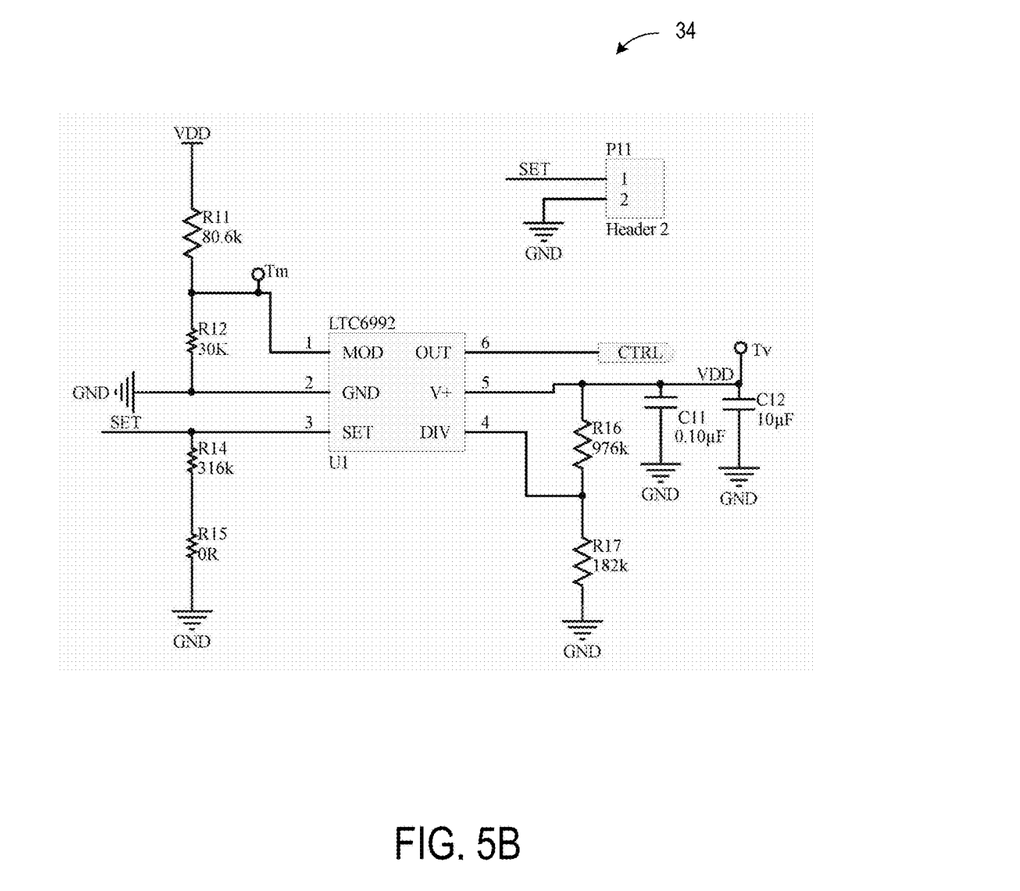
FIG. 5B shows a circuit diagram of a modulator of the first or second implementations configured as a current controlled oscillator according to one example of the present disclosure.
Figure 5C:
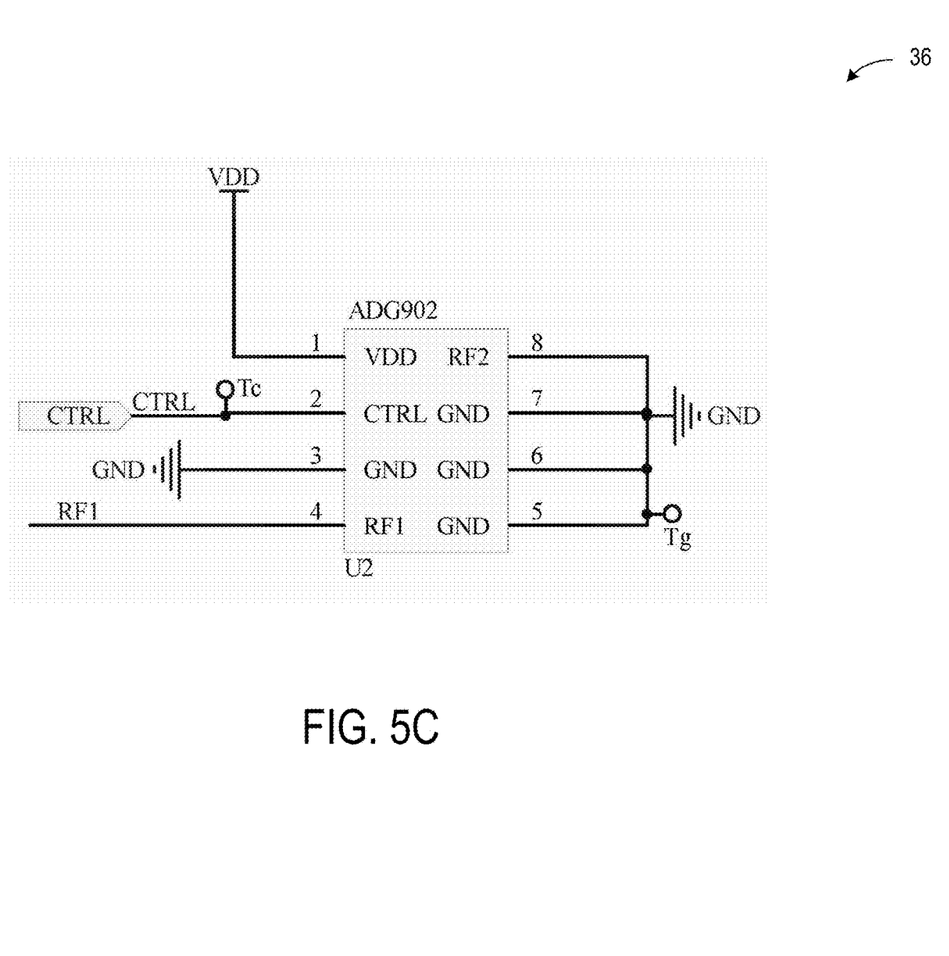
FIG. 5C shows a circuit diagram of a backscatter modulation switch of the first or second implementations configured as a junction field effect transistor (JFET) according to one example of the present disclosure.
Figure 5D:
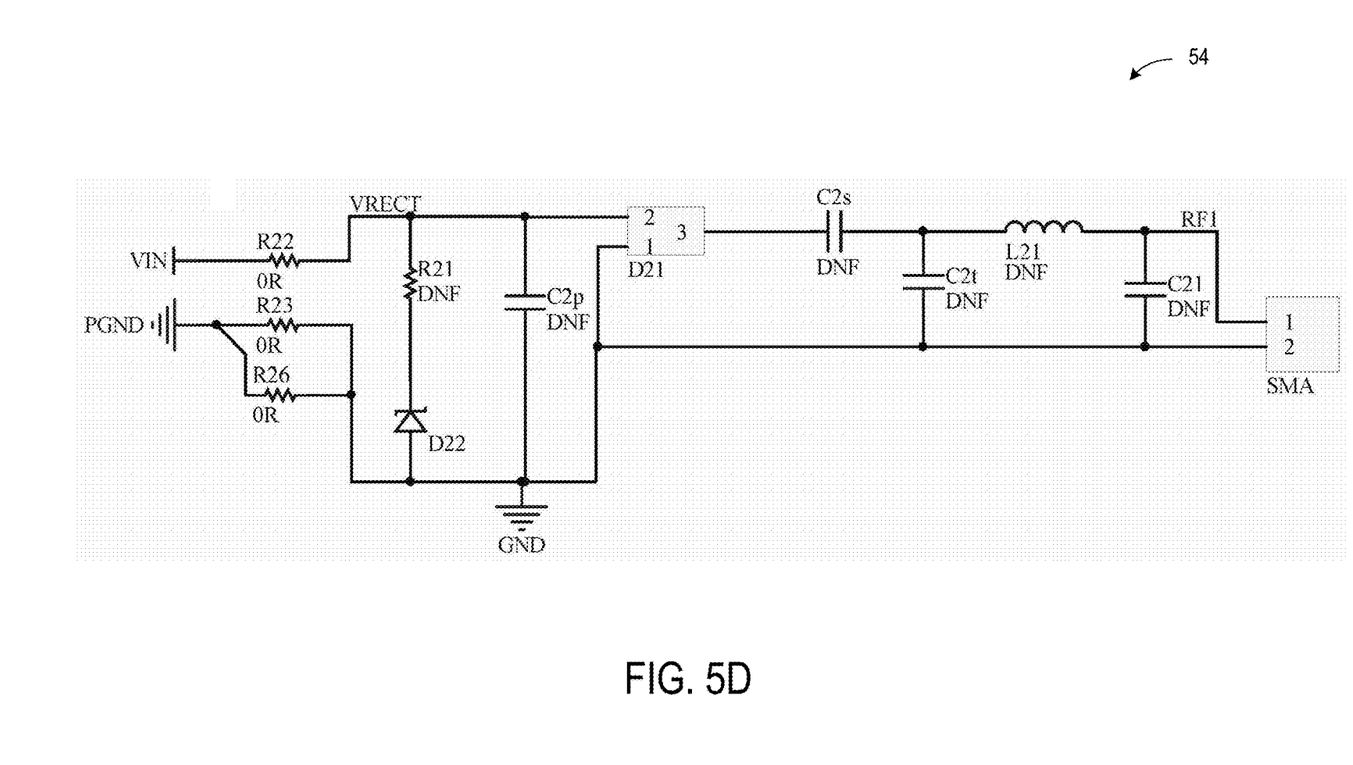
FIG. 5D shows a circuit diagram of a modulator of the first or second implementations configured as a rectifier according to one example of the present disclosure.
Figure 5E:
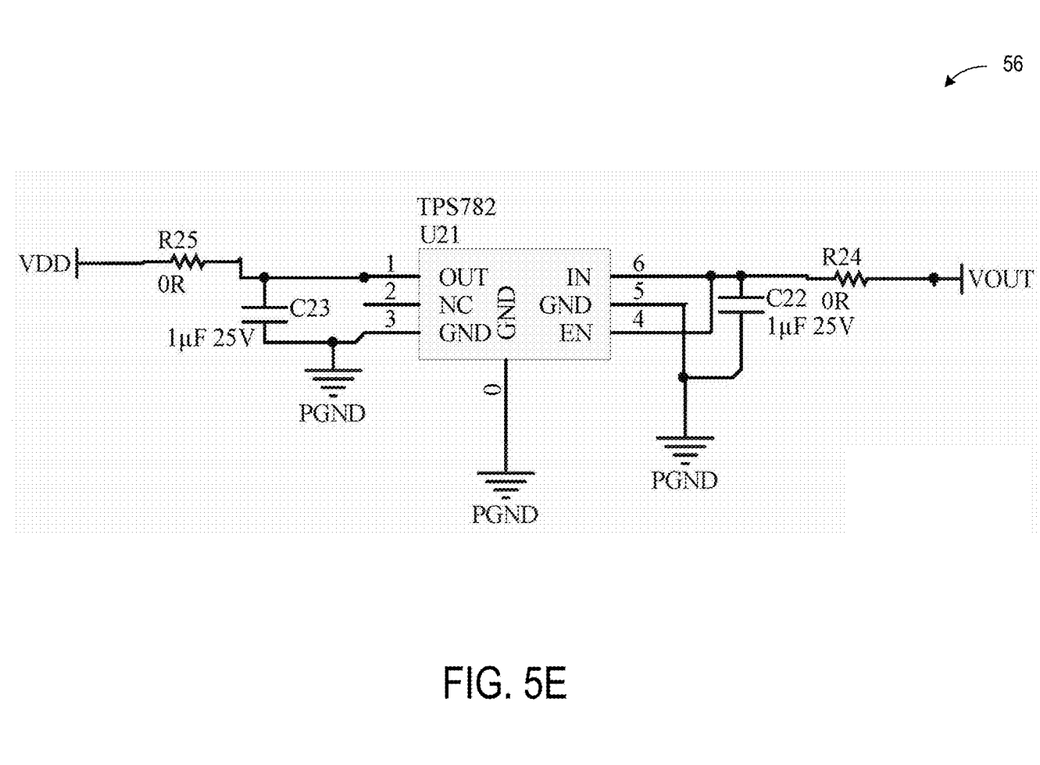
FIG. 5E shows a circuit diagram of a modulator of the first or second implementations configured as a low-dropout regulator (LDO) according to one example of the present disclosure.

FIGS. 5A-E illustrate circuit diagrams of various components that comprise the receiver devices of the first and second configurations. FIG. 5A depicts a power harvester 26 of the first implementation. FIG. 5B depicts a current controlled oscillator 34, 134 of the first or second implementations, allowing any resistive sensor to be connected. Other implementations may use a current to voltage bridge or a voltage-controlled oscillator. FIG. 5C depicts a JFET backscatter modulation switch 36, 136 of the first or second implementations. FIG. 5D depicts a rectifier 54 of the first implementation. FIG. 5E depicts a low-dropout regulator 56 of the first implementation. It will be understood that the circuit diagrams in FIGS. 5A-E are merely depicted not to be limiting, but rather to be exemplary.

In accordance with the present disclosure, a small-form factor wearable sensor platform is provided, relying upon a complex transceiver base station to simplify the sensor device. Thus, unlike conventional IOT devices, which require complicated circuitry, a receiver sensor device with simplified circuitry is provided that may incorporate a variety of possible sensors. In other words, all processing computation is moved from the receiver sensor device to the transmitter. The simplified receiver sensor device provides developers with a flexible platform for innovation, whereby developers may vary and adapt the complexity of the circuitry of the receiver sensor device for computation and processing, thereby opening the door to lowering the cost of circuitry, including microcontrollers on the device, and removing the obstacles that stand in the way of lowering size and cost of the wearable sensors. Accordingly, this platform opens the door to disposable sensors that can be easily and comfortably worn, but which still provide a rich sensor data stream. Possible applications in consumer health wearables and medical devices are boundless. Although an example of a sleep study was introduced in the present disclosure, it will be appreciated that the biomedical applications of the present disclosure are not limited to sleep studies, and may also include routine inpatient monitoring of vital signs in hospital wards and intensive care units, electroencephalography (EEG) studies to monitor seizures, electromyogram (EMG) and nerve conduction studies to monitor muscle health in patients and athletes, concussion sensors in helmets of athletes to detect and monitor concussions, etc. In obstetrics, practical applications may include fetal heart monitoring, ultrasound monitoring, intrauterine pressure catheters (IUPC), etc. By configuring the above sensor devices to be wireless sensor receiver devices in accordance with the first or second implementations of the present disclosure, medical supply costs can be lowered while raising patient comfort and convenience.

In some implementations, the methods and processes described herein may be tied to a computing system of one or more computing devices. In particular, such methods and processes may be implemented as a computer-application program or service, an application-programming interface (API), a library, and/or other computer-program product.

Figure 6:
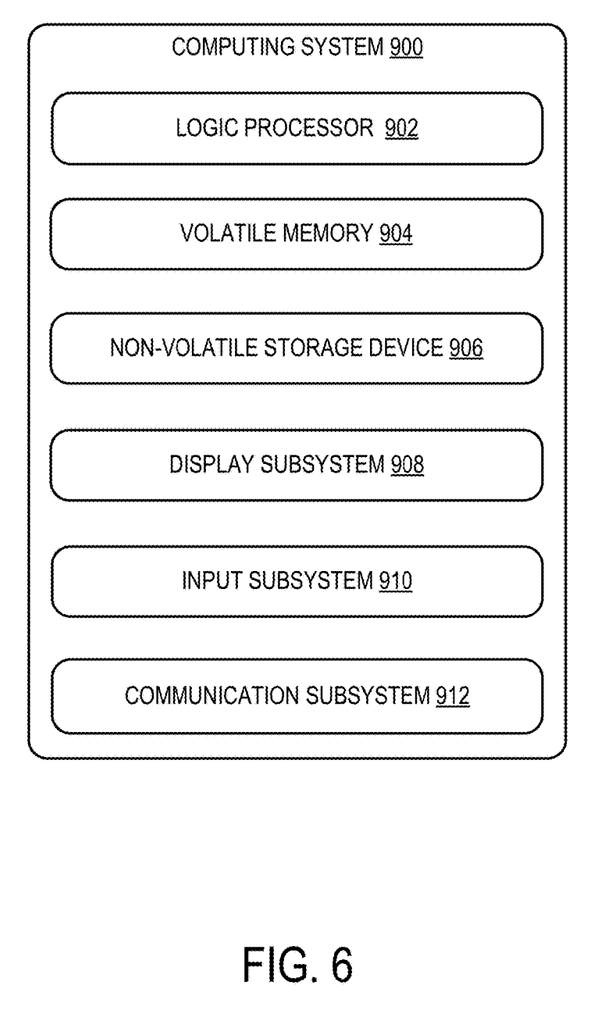
FIG. 6 shows a computing system according to an implementation of the present disclosure.

FIG. 6 schematically shows a non-limiting implementation of a computing system 900 that can enact one or more of the methods and processes described above. Computing system 900 is shown in simplified form. Computing system 900 may embody the transmitter 40 of FIG. 1 or the transmitter 140 of FIG. 2. Computing system 900 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 900 includes a logic processor 902 volatile memory 904, and a non-volatile storage device 906. Computing system 900 may optionally include a display subsystem 908, input subsystem 910, communication subsystem 912, and/or other components not shown in FIG. 6.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 906 includes one or more physical devices configured to hold instructions executable by the logic processors to implement the methods and processes described herein. When such methods and processes are implemented, the state of non-volatile storage device 906 may be transformed—e.g., to hold different data.

Non-volatile storage device 906 may include physical devices that are removable and/or built-in. Non-volatile storage device 906 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 906 may include nonvolatile, dynamic, static, read/write, read-only, sequential-access, location-addressable, file-addressable, and/or content-addressable devices. It will be appreciated that non-volatile storage device 906 is configured to hold instructions even when power is cut to the non-volatile storage device 906.

Volatile memory 904 may include physical devices that include random access memory. Volatile memory 904 is typically utilized by logic processor 902 to temporarily store information during processing of software instructions. It will be appreciated that volatile memory 904 typically does not continue to store instructions when power is cut to the volatile memory 904.

Aspects of logic processor 902, volatile memory 904, and non-volatile storage device 906 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 900 typically implemented in software by a processor to perform a particular function using portions of volatile memory, which function involves transformative processing that specially configures the processor to perform the function. Thus, a module, program, or engine may be instantiated via logic processor 902 executing instructions held by non-volatile storage device 906, using portions of volatile memory 904. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 908 may be used to present a visual representation of data held by non-volatile storage device 906. The visual representation may take the form of a graphical user interface (GUI). As the herein described methods and processes change the data held by the non-volatile storage device, and thus transform the state of the non-volatile storage device, the state of display subsystem 908 may likewise be transformed to visually represent changes in the underlying data. Display subsystem 908 may include one or more display devices utilizing virtually any type of technology. Such display devices may be combined with logic processor 902, volatile memory 904, and/or non-volatile storage device 906 in a shared enclosure, or such display devices may be peripheral display devices.

When included, input subsystem 910 may comprise or interface with one or more user-input devices such as a keyboard, mouse, touch screen, or game controller. In some implementations, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 912 may be configured to communicatively couple various computing devices described herein with each other, and with other devices. Communication subsystem 912 may include wired and/or wireless communication devices compatible with one or more different communication protocols. As non-limiting examples, the communication subsystem may be configured for communication via a wireless telephone network, or a wired or wireless local- or wide-area network, such as Bluetooth and HDMI over Wi-Fi connection. In some implementations, the communication subsystem may allow computing system 900 to send and/or receive messages to and/or from other devices via a network such as the Internet.

The following paragraphs provide additional support for the claims of the subject application. One aspect provides a wearable radio frequency receiver device comprising a receiver antenna configured to receive an interrogation signal from a transmitter; a sensor coupled to the receiver antenna and configured to receive a physiological input from a user wearing the device and generate a sensor signal based on the physiological input; and a modulator configured to perform direct modulation on the received interrogation signal based on the sensor signal, the receiver antenna being configured to reflect at least a portion of the directly modulated interrogation signal as backscatter radiation. In this aspect, additionally or alternatively, the modulation may be selected from the group consisting of frequency modulation, amplitude modulation, and phase modulation. In this aspect, additionally or alternatively, the modulation may be frequency modulation that is accomplished by frequency-shift keying. In this aspect, additionally or alternatively, the device may further comprise an adhesive pad configured to adhere to a skin of the user, the receiver antenna being configured to be embedded within the adhesive pad. In this aspect, additionally or alternatively, the device may further comprise a backscatter modulation switch configured to switch the receiver in one of two configurations: an open configuration and a short configuration. In this aspect, additionally or alternatively, the backscatter modulation switch may be one of a JFET and a MOSFET. In this aspect, additionally or alternatively, the modulator may be a voltage-controlled or current-controlled oscillator configured to control an oscillation frequency of the received interrogation signal based upon the sensor signal. In this aspect, additionally or alternatively, the sensor may be one of a variable impedance sensor, variable capacitance sensor, variable voltage sensor, variable resistance sensor or variable current sensor. In this aspect, additionally or alternatively, the device may further comprise a power harvester and/or a charge storage operatively coupled to the sensor and configured to harvest electrical power from the interrogation signal and at least temporarily store the electrical power, to thereby provide electrical power to the sensor. In this aspect, additionally or alternatively, the power harvester may include a capacitor; and/or the charge storage may include a battery and/or a capacitor. In this aspect, additionally or alternatively, the device may further comprise a receiver front end configured to receive the interrogation signal from the antenna and electrically process the interrogation signal, the receiver front end comprising at least one of a band-pass filter, a radiofrequency amplifier, a local oscillator, and/or a mixer.

Another aspect provides a sensor system comprising a transceiver including a transceiver processor configured to execute a modulation receiver, and a transceiver antenna configured to transmit an interrogation signal generated by the modulation receiver; and a wearable radio frequency receiver device including a receiver antenna configured to receive the interrogation signal from the transceiver antenna, a sensor coupled to the receiver antenna and configured to receive a physiological input from a user wearing the device and generate a sensor signal based on the physiological input, and a modulator configured to perform direct modulation on the received interrogation signal based on the sensor signal to encode the physiological input in the directly modulated interrogation signal, the receiver antenna being configured to reflect at least a portion of the directly modulated interrogation signal as backscatter radiation; and the transceiver antenna being configured to receive the directly modulated interrogation signal, and the modulation receiver is configured to process the directly modulated interrogation signal and output a decoded physiological input. In this aspect, additionally or alternatively, the modulation may be selected from the group consisting of frequency modulation, amplitude modulation, and phase modulation. In this aspect, additionally or alternatively, the modulation may be frequency modulation that is accomplished by frequency-shift keying. In this aspect, additionally or alternatively, the receiver device may further comprise a flexible substrate, and the receiver antenna, sensor, and modulator are coupled to the flexible substrate. In this aspect, additionally or alternatively, the flexible substrate may include an adhesive layer configured to releasably adhere to the skin or clothes of the user. In this aspect, additionally or alternatively, the backscatter modulation switch may be one of a JFET and a MOSFET. In this aspect, additionally or alternatively, the modulator may be a voltage-controlled or current-controlled oscillator configured to control an oscillation frequency of the received interrogation signal based upon the sensor signal. In this aspect, additionally or alternatively, the sensor may be one of a variable impedance sensor, variable capacitance sensor, variable voltage sensor, variable resistance sensor or variable current sensor.

Another aspect provides a sensor system comprising a transceiver including a transceiver processor and a transceiver antenna configured to transmit an interrogation signal generated by the processor; and a wearable radio frequency receiver device including a receiver antenna configured to receive the interrogation signal from the transceiver antenna, a sensor coupled to the receiver antenna and configured to receive a physiological input from a user wearing the device and generate a sensor signal based on the physiological input, and a modulator configured to perform direct modulation on the received interrogation signal based on the sensor signal to encode the physiological input in the directly modulated interrogation signal, the receiver antenna being configured to reflect at least a portion of the directly modulated interrogation signal as backscatter radiation; and the transceiver antenna being configured to receive the directly modulated interrogation signal, and the processor being configured to process the directly modulated interrogation signal and output a decoded physiological input.

It will be understood that the configurations and/or approaches described herein are exemplary in nature, and that these specific implementations or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A wearable radio frequency receiver device, comprising:
   a receiver radio antenna configured to receive an interrogation signal from a transmitter;
   a sensor coupled to the receiver radio antenna and configured to receive a physiological input from a user wearing the device and generate an analog sensor signal based on the physiological input; and
   a modulator configured to perform direct frequency modulation on the received interrogation signal based on the analog sensor signal so as to generate a directly frequency modulated interrogation signal carrying an analog response, wherein
   the receiver radio antenna is configured to emit at least a portion of the directly frequency modulated interrogation signal as reflected backscatter radiation carrying the analog response.

2. The device of claim 1, wherein
   the modulation is frequency modulation that is accomplished by frequency-shift keying.

3. The device of claim 1, further comprising:
   an adhesive pad configured to adhere to a skin of the user, wherein
   the receiver radio antenna is configured to be embedded within the adhesive pad.

4. The device of claim 1, further comprising:
   a backscatter modulation switch configured to switch the receiver in one of two configurations: an open configuration and a short configuration.

5. The device of claim 4, wherein
   the backscatter modulation switch is one of a JFET and a MOSFET.

6. The device of claim 1, wherein
   the modulator is a voltage-controlled or current-controlled oscillator configured to control an oscillation frequency of the received interrogation signal based upon the sensor signal.

7. The device of claim 1, wherein
   the sensor is one of a variable impedance sensor, variable capacitance sensor, variable voltage sensor, variable resistance sensor or variable current sensor.

8. The device of claim 1, further comprising:
   a power harvester and/or a charge storage operatively coupled to the sensor and configured to harvest electrical power from the interrogation signal and at least temporarily store the electrical power, to thereby provide electrical power to the sensor.

9. The device of claim 8, wherein
the power harvester includes a capacitor; and/or
the charge storage includes a battery and/or a capacitor.

10. The device of claim 1, further comprising:
a receiver front end configured to receive the interrogation signal from the antenna and electrically process the interrogation signal, the receiver front end comprising at least one of a band-pass filter, a radiofrequency amplifier, a local oscillator, and/or a mixer.

11. A sensor system, comprising:
a transceiver including a transceiver processor configured to execute a modulation receiver, and a transceiver antenna configured to transmit an interrogation signal generated by the modulation receiver; and
a wearable radio frequency receiver device including a receiver radio antenna configured to receive the interrogation signal from the transceiver antenna, a sensor coupled to the receiver radio antenna and configured to receive a physiological input from a user wearing the device and generate an analog sensor signal based on the physiological input, and a modulator configured to perform direct frequency modulation on the received interrogation signal based on the analog sensor signal so as to generate a directly frequency modulated interrogation signal carrying an analog response, to encode the physiological input in the directly frequency modulated interrogation signal, wherein the receiver radio antenna is configured to emit at least a portion of the directly frequency modulated interrogation signal as reflected backscatter radiation carrying the analog response, wherein
the transceiver antenna is configured to receive the directly frequency modulated interrogation signal, and the modulation receiver is configured to process the directly frequency modulated interrogation signal and output a decoded physiological input.

12. The system of claim 11, wherein
the modulation is frequency modulation that is accomplished by frequency-shift keying.

13. The system of claim 11, wherein
the receiver device further comprises a flexible substrate, and the receiver radio antenna, sensor, and modulator are coupled to the flexible substrate.

14. The system of claim 13, wherein the flexible substrate includes an adhesive layer configured to releasably adhere to the skin or clothes of the user.

15. The system of claim 11, further comprising:
a backscatter modulation switch configured to switch the receiver in one of two configurations: an open configuration and a short configuration, wherein
the backscatter modulation switch is one of a JFET and a MOSFET.

16. The system of claim 11, wherein
the modulator is a voltage-controlled or current-controlled oscillator configured to control an oscillation frequency of the received interrogation signal based upon the sensor signal.

17. The system of claim 11, wherein
the sensor is one of a variable impedance sensor, variable capacitance sensor, variable voltage sensor, variable resistance sensor or variable current sensor.

18. A sensor system comprising:
a transceiver including a transceiver processor and a transceiver antenna configured to transmit an interrogation signal generated by the processor; and
a wearable radio frequency receiver device including a receiver radio antenna configured to receive the interrogation signal from the transceiver antenna, a sensor coupled to the receiver radio antenna and configured to receive a physiological input from a user wearing the device and generate an analog sensor signal based on the physiological input, and a modulator configured to perform direct frequency modulation on the received interrogation signal based on the analog sensor signal so as to generate a directly frequency modulated interrogation signal carrying an analog response, to encode the physiological input in the directly frequency modulated interrogation signal, wherein the receiver radio antenna is configured to emit at least a portion of the directly frequency modulated interrogation signal as reflected backscatter radiation carrying the analog response, wherein
the transceiver antenna is configured to receive the directly frequency modulated interrogation signal, and the processor is configured to process the directly frequency modulated interrogation signal and output a decoded physiological input.

* * * * *